(12) United States Patent
Li et al.

(10) Patent No.: US 11,879,322 B2
(45) Date of Patent: Jan. 23, 2024

(54) COMPREHENSIVE THREE-DIMENSIONAL EXPLOITATION EXPERIMENTAL SYSTEM FOR LARGE-SCALE AND FULL-SIZED EXPLOITATION WELLS

(71) Applicant: GUANGZHOU INSTITUTE OF ENERGY CONVERSION, CHINESE ACADEMY OF SCIENCES, Guangzhou (CN)

(72) Inventors: Xiaosen Li, Guangzhou (CN); Yi Wang, Guangzhou (CN); Zhaoyang Chen, Guangzhou (CN); Zhiming Xia, Guangzhou (CN); Yu Zhang, Guangzhou (CN); Gang Li, Guangzhou (CN)

(73) Assignee: GUANGZHOU INSTITUTE OF ENERGY CONVERSION, CHINESE ACADEMY OF SCIENCES, Guangzhou (CN)

( * ) Notice: Subject to any disclaimer, the term of this patent is extended or adjusted under 35 U.S.C. 154(b) by 607 days.

(21) Appl. No.: 17/251,501

(22) PCT Filed: Sep. 8, 2020

(86) PCT No.: PCT/CN2020/114092
§ 371 (c)(1),
(2) Date: Dec. 11, 2020

(87) PCT Pub. No.: WO2021/159697
PCT Pub. Date: Aug. 19, 2021

(65) Prior Publication Data
US 2022/0235646 A1    Jul. 28, 2022

(30) Foreign Application Priority Data
Aug. 6, 2020 (CN) .......................... 202010784465.6

(51) Int. Cl.
*E21B 47/002* (2012.01)
*E21B 34/06* (2006.01)
(Continued)

(52) U.S. Cl.
CPC ............ *E21B 47/002* (2020.05); *E21B 34/06* (2013.01); *E21B 41/0099* (2020.05);
(Continued)

(58) Field of Classification Search
None
See application file for complete search history.

(56) References Cited

U.S. PATENT DOCUMENTS

| 2015/0205004 A1* | 7/2015 | Li | ........................ G01V 99/005 703/10 |
| 2016/0305205 A1* | 10/2016 | Li | ........................ E21B 34/00 |
| 2018/0172574 A1* | 6/2018 | Li | ........................ B01J 3/03 |

FOREIGN PATENT DOCUMENTS

CN           102305052 A        1/2012

* cited by examiner

*Primary Examiner* — Kristina M Deherrera
*Assistant Examiner* — Mark A Shabman
(74) *Attorney, Agent, or Firm* — Bayramoglu Law Offices LLC (57) ABSTRACT

A comprehensive three-dimensional exploitation experimental system for large-scale and full-sized exploitation wells includes a reactor, configured to prepare a natural gas hydrate sample, for simulating an environment for forming a natural gas hydrate reservoir in seafloor sediments. The reactor includes a reactor body, an upper cover disposed at an upper surface of the reactor body, and a lower cover disposed at a lower surface of the reactor body; a gas introducing module, configured to introduce gas to the reactor during hydrate formation; a liquid introducing module, configured to introduce liquid to the reactor during hydrate formation; a temperature regulating module, con-
(Continued)

figured to regulate a temperature in the reactor; a data collecting-processing-displaying module, configured to collect, store, process and display data of the comprehensive three-dimensional exploitation experimental system during an experiment.

18 Claims, 6 Drawing Sheets (51) Int. Cl.
*E21B 43/01* (2006.01)
*E21B 47/06* (2012.01)
*E21B 41/00* (2006.01)
(52) U.S. Cl.
CPC .............. *E21B 43/01* (2013.01); *E21B 47/06* (2013.01); *E21B 2200/04* (2020.05)

COMPREHENSIVE THREE-DIMENSIONAL EXPLOITATION EXPERIMENTAL SYSTEM FOR LARGE-SCALE AND FULL-SIZED EXPLOITATION WELLS

CROSS REFERENCE TO THE RELATED APPLICATIONS

This application is the national stage entry of International Application No. PCT/CN2020/114092, filed on Sep. 8, 2020, which is based upon and claims priority to Chinese Patent Application No. 202010784465.6, filed on Aug. 6, 2020, the entire contents of which are incorporated herein by reference.

TECHNICAL FIELD

The present invention relates to the field of natural gas hydrate exploitation, and particularly relates to a comprehensive three-dimensional exploitation experimental system for large-scale and full-sized exploitation wells.

BACKGROUND

Deep-sea oil and gas resources are considered to be an important field in the petroleum industry. Exploitation of deep-water and ultra-deep-water oil and gas resources has attracted much attention in developed countries such as the United States and Britain. Generally, it is believed that natural gas hydrate resources deposited 1-3 km under the seafloor is an unconventional resource that has huge unexploited reserves and one of the most potential alternative energy sources in the 21st century. The great energy potential has attracted countries over the world to go deeper in the research of survey, experimental exploitation, and environmental impact assessment. The United States, Canada, Germany, Norway, and neighboring countries such as Japan, India, South Korea, and Vietnam have all established long-term gas hydrate research plans.

As hydrate research goes deeper, experimental devices for simulating hydrate formation and exploitation have been developed. For example, the patent literature CN102305052A discloses experimental device and method for three-dimensional multi-well exploitation of natural gas hydrates, wherein the device realizes the simulation of multi-well exploitation of hydrates, thereby developing the three-dimensional simulation experiments, and providing experimental foundation and basis for large-scale exploitation of natural gas hydrates. However, as the research keeps going deeper, requirements on the devices are getting higher and higher. Currently, the requirements on experimental simulation devices for natural gas hydrates generally comprise the following:

(1) Higher Comprehensiveness

As scientific research goes deeper, it will develop from a single-disciplinary form to an interdisciplinary and integrated form. Demands on experimental devices for natural gas hydrate simulation have also been developed from single-function designs to integration and systematization. Investigations shows that, existing experimental devices for natural gas hydrate simulation are capable of not only simulating the phase behavior of hydrates, but also simulating hydrate sediments, determining various physical and chemical properties of stratum with or without hydrate formation, and studying geological parameters of hydrate formation.

(2) Higher Visual Performance

With the development of macroscopic research to a certain extent, it is no longer sufficient to explain active physical phenomena. In order to analyze and understand the various characteristics of natural gas hydrates as clearly as possible, higher functional requirements are raised on the experimental simulation systems, to realize visual inspection of various phase change processes of natural gas hydrates, such as the formation, accumulation, and dissociation, and even, to enable the observation, recording and analysis to the research object in microcosmic scale through other devices.

(3) More Severe Conditions for Experimental Simulation

As more samples collected from deeper regions, the understanding on formation environment for hydrate reservoirs has become clearer, which imposes new challenges to the experimental simulation devices. Huge pressure and low ambient temperature are necessary for the formation of natural gas hydrates, and thus higher requirements are raised on the experimental simulation systems for producing such conditions. How to accurately regulate the simulation environment, how to ensure the normal operation of each experimental device under severe conditions, and how to ensure the high structural reliability of the experimental devices under such conditions, have been of great consideration for the design and development of experimental systems.

(4) Higher Accuracy

Higher requirements on measurement performance of the experimental simulation systems have been raised for accurately understanding the impact of hydrate formation status and exploitation means on the stratum, precisely reflecting various characteristics of gas hydrates in the formation, and studying various mechanisms and relationships. High-accuracy measurement and high-accuracy control are necessary for accurate simulation. In order to realize such requirements, in addition to the use of reliable and accurate sensors, higher requirements are also raised on the design. Reasonable arrangement and use of various components and equipment such as sensors are also key factors that affect the measurement accuracy of the experimental simulation devices.

SUMMARY

In order to meet at least one of the above-mentioned requirements, the present invention provides a comprehensive three-dimensional exploitation experimental system for large-scale and full-sized exploitation wells.

In order to realize the above object, the technical solution of the present invention involves; A comprehensive three-dimensional exploitation experimental system for large-scale and full-sized exploitation wells, comprises:

a reactor, configured to prepare a natural gas hydrate sample, for simulating environment for forming a natural gas hydrate reservoir in seafloor sediments, wherein the reactor comprises a reactor body, an upper cover disposed at an upper surface of the reactor body, and a lower cover disposed at a lower surface of the reactor body;

a gas introducing module, configured to introduce gas to the reactor during hydrate formation;

a liquid introducing module, configured to introduce liquid to the reactor during hydrate formation;

a temperature regulating module, configured to regulate a temperature in the reactor;

a data collecting-processing-displaying module, configured to collect, store, process and display data of the exploitation experimental system during an experiment.

Furthermore, a central vertical well is disposed at a center and throughout a vertical direction of the reactor, and holes are spacedly disposed on the central vertical well along a longitudinal direction of the central vertical well inside the reactor; a directional-control ball valve is disposed at an upper portion of the central vertical well outside the reactor, and one outlet of the directional-control ball valve is connected with a central vertical well discharge pipeline; a sight glass is provided on the central vertical well discharge pipeline, wherein a first camera and a first lamp are provided beside the sight glass;

an endoscopic-camera tube is disposed inside the central vertical well, passing through the directional-control ball valve, and extending to outside of the central vertical well; a second camera and a second lamp are provided at an bottom end of the endoscopic-camera tube, wherein the second lamp is disposed above the second camera and arranged obliquely;

images captured by the first camera and the second camera are sent to the data collecting-processing-displaying module;

a mechanical sensor is provided at the bottom end of the endoscopic-camera tube, wherein data measured by the mechanical sensor is sent to the data collecting-processing-displaying module;

a scaled sight glass for observing settled sands is disposed on the central vertical well and outside the reactor.

Furthermore, inside of the reactor body is divided into a plurality of layers from top to bottom, wherein a plurality of vertical wells are disposed throughout each layer, including one central vertical well located at center and non-central vertical wells being the remainders;

each of the non-central vertical well is provided with a non-central vertical well outlet pipeline, wherein each of the non-central vertical well outlet pipelines is correspondingly provided with one non-central vertical well pressure sensor, one non-central vertical well outlet valve, one differential pressure sensor, and one communicating vessel valve communicatedly in sequence, and all of the communicating vessel valves are connected with the communicating vessel; the non-central vertical well pressure sensors, the non-central vertical well outlet valves, the differential pressure sensors, and the communicating vessel valves are respectively provided in an amount identical to that of the non-central vertical wells;

the central vertical well is provided with a central vertical well outlet pipeline, wherein the central vertical well outlet pipeline is provided with a central vertical well pressure sensor and a central vertical well outlet valve communicatedly in sequence, and the central vertical well outlet valve is connected with the communicating vessel;

a data output of each of the non-central vertical well pressure sensors, the central vertical well pressure sensor, and the differential pressure sensors is connected to the data collecting-processing-displaying module;

the differential pressure sensors have a measuring accuracy higher than that of the central vertical well pressure sensor and the non-central vertical well pressure sensors, and a measuring range lower than that of the central vertical well pressure sensor and the non-central vertical well pressure sensors.

Furthermore, the communicating vessel is provided with a communicating vessel pressure sensor and a gas injection valve.

Furthermore, an upper circulation coil and a lower circulation coil are respectively disposed at an upper end and a lower end inside the reactor body, wherein the upper circulation coil and the lower circulation coil are respectively provided with an independent heat exchange device to realize the circulation of the heat transfer medium in the coils; temperature control pipes are spacedly provided, with an amount of N, inside the reactor body and between the upper circulation coil and the lower circulation coil, configured to form a vertical temperature gradient in the reactor body, wherein N is a positive integer; each temperature control pipe is also provided with an independent heat exchange device to realize the circulation of the heat transfer medium in the temperature control pipe.

Furthermore, the N temperature control pipes are equally spaced from bottom to top and a constant temperature difference is given between the temperature control pipes, wherein the temperature difference is expressed as:

$\Delta T=(T1-T2)/(N+1)$, wherein T2 represents a temperature of the lower circulation coil, and T1 represents a temperature of the upper circulation coil.

Furthermore, temperature sensors are provided inside the reactor body and configured to monitor the temperatures of the upper circulation coil, the lower circulation coil and the N temperature control pipes and transmit the monitored temperature data to a temperature regulating module; the temperature regulating module is configured to regulate in real time the operation of each heat exchange device according to the monitored temperature data, so as to maintain the vertical temperature gradient in the reactor body stable.

Furthermore, the layers inside the reactor body include a superstratum layer, a sediment layer and a substratum layer from top to bottom, and a displacement sensor fixing plate is disposed inside the reactor body; a plurality of displacement sensors are evenly disposed wherein one end of each displacement sensor is fixed to the displacement sensor fixing plate and the other end of each displacement sensor is stretchably and sealingly fixed to a rubber piston, and the rubber piston is tightly attached to the superstratum layer; the displacement sensors are configured to send monitored data to the data collecting-processing-displaying module.

Furthermore, the rubber piston comprises a piston frame and a rubber piston plate whose periphery is sealingly fixed to the piston frame; the rubber piston further comprises a rubber insert, a piston gasket, and a clip; the piston gasket is embedded in a groove of the piston frame; the periphery of the rubber piston plate is sealingly fixed to a lower surface of the piston frame through the rubber insert; the clip is embedded in the rubber insert.

Furthermore, the comprehensive three-dimensional exploitation experimental system further comprises a gas production module; the gas production module is configured to control a depressurization range and a depressurization rate inside the reactor, and conduct gas-liquid-sand separation and measurement during hydrate exploitation;

the gas introducing module comprises a natural gas supply, a booster pump, a gas flow meter, and a gas valve which are connected sequentially, wherein an outlet of the gas valve is connected to the reactor;

the liquid introducing module comprises a liquid supply, a liquid introducing pump, a temperature regulator, and a liquid valve which are connected sequentially, wherein an outlet of the liquid valve is connected to the reactor.

Compared with the prior art, the present invention comprises the following beneficial effects:

(1) The system enables preparing a natural gas hydrate sample and simulating environment for forming a natural gas hydrate reservoir in 3,000-meter-deep seafloor sediments at South China Sea.

(2) The system allows simulation study for the depressurization method and the thermal stimulation method under various well arrangements.

(3) Exploitation researches with full-sized wells are realized for optimizing well structures and studying sand production and prevention.

(4) The system enables the study on hydrate dissociation, liquid-gas flow, heat transfer, and sediment stability mechanism.

BRIEF DESCRIPTION OF THE DRAWINGS

Reference signs: 1—reactor; 2—gas introducing module; 3—liquid introducing module; 4—data collecting-processing-displaying module; 51—natural gas supply; 52—booster pump; 53—gas flow meter; 54—gas valve; 61—liquid supply; 62—liquid introducing pump; 63—temperature regulator; 64—liquid valve.

Reference signs: 10—reactor body; 1001—superstratum layer; 1002—sediment layer; 1003—substratum layer; 11—upper cover; 12—lower cover; 13—central vertical well; 131—hole; 132—scaled sight glass for observing settled sands; 14—directional-control ball valve; 15—central vertical well discharge pipeline; 151—sight glass; 16—first camera; 17—endoscopic-camera tube; 18—second camera; 19—second lamp.

Reference signs: 30—displacement sensor fixing plate; 31—displacement sensor; 32—rubber piston; 321—piston frame; 322—rubber piston plate; 323—rubber insert; 324—piston gasket; 325—clip.

Reference signs: 20—non-central vertical well pressure sensor; 21—non-central vertical well outlet valve; 22—communicating vessel valve; 23—differential pressure sensor; 24—communicating vessel; 25—central vertical well outlet valve; 26—central vertical well pressure sensor; 27—central vertical well outlet pipeline; 28—communicating vessel pressure sensor; 29—gas injection valve; 200—non-central vertical well outlet pipeline.

Reference signs: 41—upper circulation coil; 42—lower circulation coil; 43—temperature control pipe.

DETAILED DESCRIPTION OF THE EMBODIMENTS

In the description of the present invention, it should be noted that, unless otherwise clearly specified and limited, the terms such as "provide" and "connect" should be understood in a broad sense; for example, a connection can be a fixed connection, a detachable connection, or an integration connection, it can also be a mechanical connection, an electrical connection, or a signal connection, and it can also be a direct connection, an indirect connection through an intermediate medium, or an internal connection between two components. For those of ordinary skill in the art, the specific meaning of the above terms in the present invention should be understood depending on specific circumstances. The technical solution of the present invention will be further described below in combination with the drawings and embodiments.

Reference is made to FIG. 1 to FIG. 11 that a comprehensive three-dimensional exploitation experimental system for large-scale and full-sized exploitation wells comprises: a reactor 1, a gas introducing module 2, a liquid introducing module 3, a temperature regulating module, and a data collecting-processing-displaying module 4.

Figure 1:
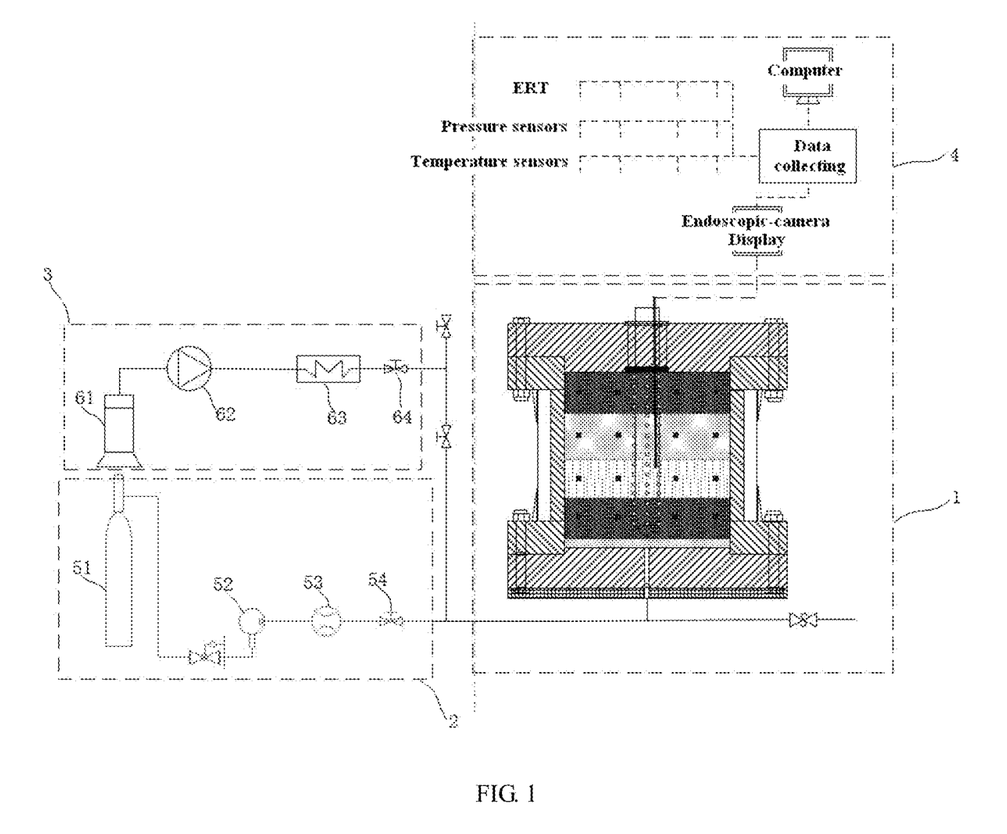
FIG. 1 shows the framework of a comprehensive three-dimensional exploitation experimental system in one embodiment.

The reactor 1 is configured to prepare a natural gas hydrate sample for simulating environment (including temperature, pressure, sediments, and gas-water-hydrate saturation level) for forming a natural gas hydrate reservoir in 3,000-meter-deep seafloor sediments at South China Sea, and operate in combination with other modules to realize other functions. Inside the reactor 1 is divided into a superstratum layer 1001, a sediment layer 1002 and a substratum layer 1003 from top to bottom. The reactor 1 comprises a reactor body 10, an upper cover 11 disposed at an upper surface of the reactor body 10, and a lower cover 12 disposed at a lower surface of the reactor body 10. The reactor body 10 has an internal volume of 2,500 L, a working pressure range of 0 to 30 MPa (accuracy: ±0.1 MPa), and a working temperature range of −15° C. to 130° C. (accuracy: ±0.5° C.). The reactor body 10 is made of high strength alloy steel and subjected to stainless steel resurfacing inside. The reactor covers are designed as flat closures using flange connection.

Specifically, the gas introducing module 2 comprises a natural gas supply 51, a booster pump 52, a gas flow meter 53, and a gas valve 54 which are connected sequentially, wherein an outlet of the gas valve 54 is connected to the reactor 1. The liquid introducing module 3 comprises a liquid supply 61, a liquid introducing pump 62, a temperature regulator 63, and a liquid valve 64 which are connected sequentially, wherein an outlet of the liquid valve 64 is connected to the reactor 1. By introducing natural gas and liquid to the reactor from the gas introducing module 2 and the liquid supply 61, the natural gas hydrate sample is prepared in the reactor. The comprehensive three-dimensional exploitation experimental system further comprises a gas production module; the gas production module is configured to control a depressurization range and a depressurization rate inside the reactor, and conduct gas-liquid-sand separation and measurement during hydrate exploitation.

As the existing technology does not allow the visual observation of the formation of natural gas hydrates inside the reactor, at present in the field of natural gas hydrate, visual observation technology is developed for the purpose of inspecting the formation, distribution, and dissociation of natural gas hydrates, which is realized by disposing a sight glass on the wall of a reactor, introducing a camera into the central vertical well and towards the reactor to film the distribution of hydrates in porous media, providing transparent water bath and reactor for small-scale experiment, or using imaging technologies such as XRD and CT. It is difficult to film the distribution of hydrates in porous media, since the hydrates are covered by the media. Transparent reactors are expensive, thus not suitable for most conditions. The X-ray CT imaging technology relies on the density variations inside the measured object, while hydrates are mainly composed of natural gas (mainly methane molecules) and water molecules which are similar in molecular weight and thus cannot be distinguished by X-ray CT, resulting in low accuracy for imaging the phase state of natural gas hydrates. The use of camera in the central vertical well is still an immature technology. Furthermore, the visual inspection of several properties during hydrate exploitation, such as multiphase flow and sand production, inside the central vertical well, is still not realized; the existing systems do not allow the real-time observation of outlet flow; the visual observation and measurement of settled sands are ignored.

Figure 2:
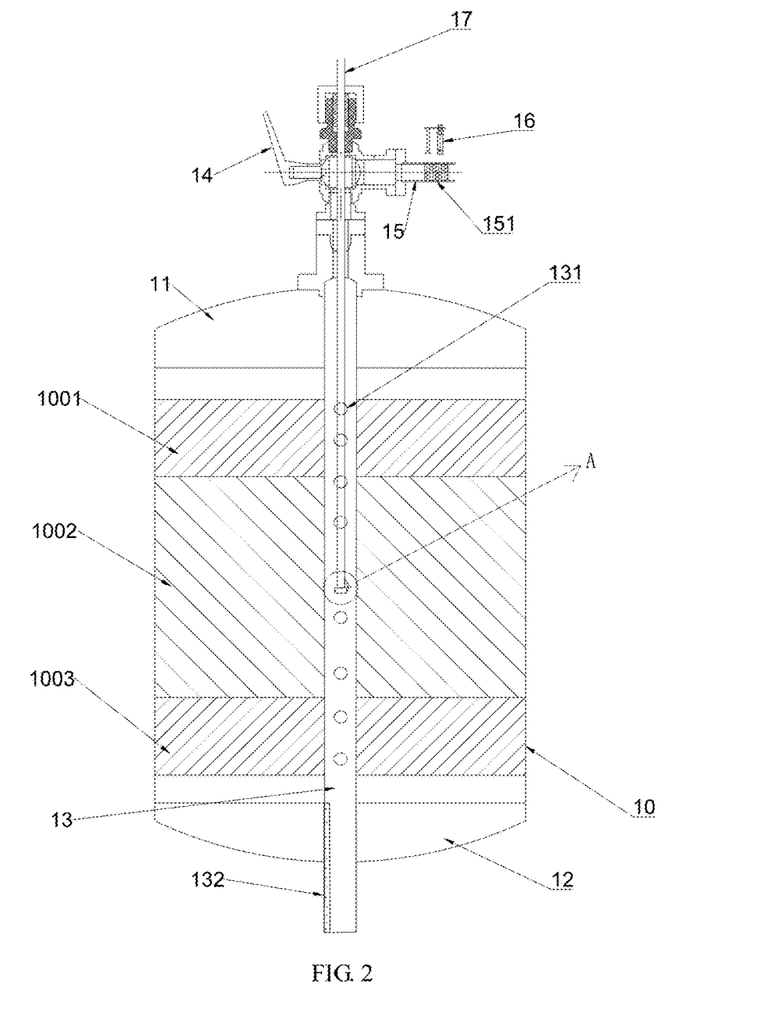
FIG. 2 shows the structure of a reactor in an embodiment allowing visual observation.
Figure 3:
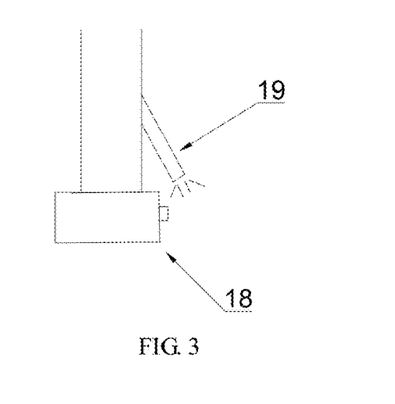
FIG. 3 is an enlarged view of area A in FIG. 2

Accordingly, in some embodiments, as shown in FIG. 2 and FIG. 3, a central vertical well 13 is disposed at a center and throughout a vertical direction of the reactor 1, and holes 131 are spacedly disposed on the central vertical well 13 along a longitudinal direction of the central vertical well 13 inside the reactor 10. A directional-control ball valve 14 is disposed at an upper portion of the central vertical well 13 outside the reactor 1, and one outlet of the directional-control ball valve 14 is connected with a central vertical well discharge pipeline 15, such that it is possible to alter the fluid flow direction inside the central vertical well 13 via the directional-control ball valve 14 and thereby the pipe flow from the central vertical well 13 will be directed to the central vertical well discharge pipeline 15. A sight glass 151 is provided on the central vertical well discharge pipeline 15, wherein a first camera 16 and a first lamp beside the sight glass 151 for filming the pipe flow inside the central vertical well discharge pipeline 15, such that the first camera 16 enables the real-time monitoring of the discharging pipe flow from the central vertical well 13, and thereby realizes the visual inspection on the horizontal pipe flow coming out from the central vertical well 13, which gives flow information of the discharge pipeline during hydrate exploitation, such as: whether the pipe flow contains hydrates, whether the pipe flow contains sands, and sand diameters.

Inside the central vertical well 13 is further provided with an endoscopic-camera tube 17, which is disposed inside the central vertical well 13, passing through the directional-control ball valve 14 and extending to the outside of the central vertical well 13, such that the endoscopic-camera tube 17 is able to move up and down and rotate 360 degrees inside the central vertical well 13. As shown in FIG. 3, a second camera 18 and a second lamp 19 are provided at the bottom end of the endoscopic-camera tube 17, wherein the second lamp 19 is disposed above the second camera 18 and arranged obliquely, so that the second camera 18 takes clearer videos. Accordingly, by moving the endoscopic-camera tube 17, the second camera 18 and the second lamp 19 can move up and down along with the endoscopic-camera tube 17 inside the central vertical well 13; also, the second camera 18 and the second lamp 19 can rotate 360 degrees. During hydrate exploitation, the visual inspection on the multiphase flow and sand production at any layer and any position can be realized, by moving the second camera 18 and the second lamp 19 with the endoscopic-camera tube 17 to the specific position, where they aim at the hole 131 of the desired position, and the second lamp 19 provides an oblique light source to help the second camera 18 work. Accordingly, the situation of sand production of each layer can be inspected, such as the sand production time, the occurrence of sand blast, and the volume of sands; also, the camera can rotate to aim at different holes, for observing the situation at each single hole, such as sand production rate and gas production rate. Meanwhile, the second camera 18 and the second lamp 19 can move to where they are required during experiment; they will be moved to the designated observation position when they are needed, while they will be moved to a space above the directional-control ball valve 14 when they are not needed so as to prevent them from affecting the vertical pipe flow and also protect the camera. Moreover, the endoscopic-camera tube can be further provided with other measurement devices, such as an infrared-based device or an ultrasound-based device for measuring the flow rate, to obtain more information inside the central vertical well.

In addition, the endoscopic-camera tube 17 can be further provided at its bottom end with a mechanical sensor (not shown in the drawings) which sends the monitored data to the data collecting-processing-displaying module 4, such that during sand blast, the mechanical sensor can send sand information to the data collecting-processing-displaying module 4 for analysis, giving information such as sand sizes, and thereby realizing the visual inspection of sands. In addition, the central vertical well 13 can be further provided, at its section outside the reactor, with a scaled sight glass 132 for observing settled sands, which is made of sapphire and allows observing the amount of settle sands at the bottom of the central vertical well.

During hydrate exploitation, the visual inspection on the multiphase flow and sand production at any layer and any position can be realized, by moving the second camera and the second lamp using the endoscopic-camera tube to the specific position where they aim at the hole of the desired position, so as to realize the real-time inspection on the sand production, gas production, and multiphase flow inside the central vertical well.

With the aid of the first lamp, the first camera realizes the real-time monitoring of discharged pipe flow.

The first camera and the second camera send the captured videos to the data collecting-processing-displaying module, so as to enable the visual inspection inside the central vertical well. During the visual inspection of sand blast, the mechanical sensor sends the sand information to the data collecting-processing-displaying module for analysis to give sand sizes, realizing the visual inspection of sands.

The second camera and the second lamp will be moved to a space above the directional-control ball valve when they are not needed, where they will be protected after the directional-control ball valve is switched.

Accordingly, the above-mentioned equipments provided to the reactor allow the visual inspection of natural gas hydrate production, taking videos inside the central vertical well, real-time inspection on the multiphase flow inside the central vertical well including whether the flow contains hydrate phase and how the flow rate changes. They also allow inspect the sand production of different formation layers, including the sand production time, the occurrence of sand blast, and the volume of sands. They can move to where they are required during experiment; they will be moved to the designated observation position when they are needed, while they will be moved to a space above the directional-control ball valve when they are not needed so as to prevent them from affecting the vertical pipe flow and also protect the camera. They also enable the visual inspection on the horizontal pipe flow coming out from the central vertical well, which gives flow information of the discharge pipeline during hydrate exploitation, such as: whether the pipe flow contains hydrates, whether the pipe flow contains sands, and sand diameters. They also enable the inspection of pipe flow of gas phase and water phase.

Accordingly, compared with the prior art, the technical solution as shown in FIG. 2 to FIG. 3 has the following technical advantages:

(1) Visual inspection inside the central vertical well is realized.

(2) It is possible to conduct real-time inspection on the multiphase flow inside the central vertical well including whether the flow contains hydrate phase and how the flow rate changes.

(3) It is possible to inspect the sand production of different formation layers, including the sand production time, the occurrence of sand blast, and the volume of sands.

(4) By taking advantage of the mobility and 360° rotatability of the camera, it is possible to take photos or videos of a particular region, allowing inspecting the sand production rate and gas production rate of a specific hole.

(5) The camera can be moved to where it is required during experiment; it will be moved to the designated observation position when needed, while it will be moved to a space above the directional-control ball valve when not needed so as to prevent it from affecting the vertical pipe flow and also protect the camera.

(6) The camera disposed inside the central vertical well can be provided with a mechanical sensor which can be used to inspect the sand blast and multiphase flow, so as to obtain more information.

(7) Visual inspection on the settled sands at the bottom of the central vertical well is realized, allowing the observation on the settling process and the measurement of the amount of settled sands.

(8) It enables the visual inspection on the horizontal pipe flow coming out from the central vertical well, which gives flow information of the discharge pipeline during hydrate exploitation, such as: whether the pipe flow contains hydrates, whether the pipe flow contains sands, and sand diameters. They also enable the inspection of pipe flow of gas phase and water phase.

In additional, since the exploitation of natural gas hydrates will affect the mechanical behaviors of sediments, which may induce geological disasters such as stratum subsidence and slope slippage, this is a major safety issue for the exploitation of natural gas hydrates, and thus it is of great practical significance to analyze the mechanical behaviors of hydrate sediments. So far, studies on stratum deformation caused by natural gas hydrate dissociation are mostly carried out using the triaxial test method, in which the analysis of stratum deformation is realized by simulating the stratum conditions through applying axial pressure and confining pressure, and calculating the subsidence based on volume changes during hydrate dissociation. This method is effective for the analysis of stratum deformation but usually conducted through small-scale experiments. When experiments are scaled up, the method would be inapplicable since large-scale dissociation of natural gas hydrates will bring about greater deformation, which is currently one of the biggest challenges in measurement; moreover, as the reactor is scaled up, the subsidence presented in one dimension is insufficient for reflecting the irregularity of deformation during hydrate dissociation. For large-scale experimental system of natural gas hydrates, the deficiencies of existing technology mainly include: it is impossible to measure the stratum deformation throughout a large area; it is impossible to measure a large-scale stratum deformation; it is difficult to conduct the measurements of stratum deformation in more than one dimension.

Figure 4:
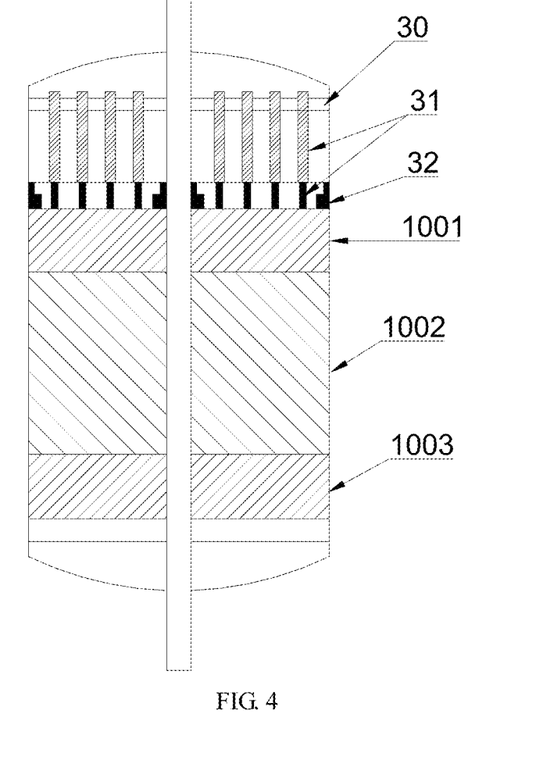
FIG. 4 is a sectional view of a reactor in another embodiment.
Figure 5:
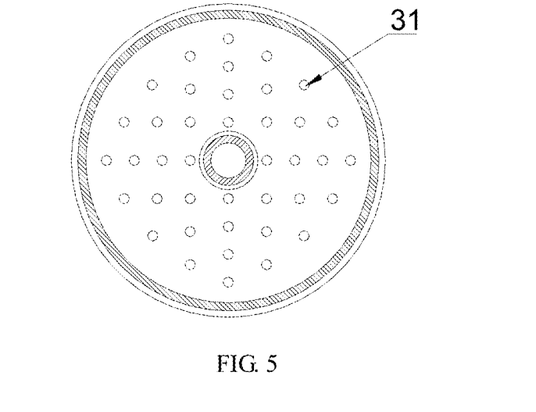
FIG. 5 shows the distribution of displacement sensors.
Figure 6:
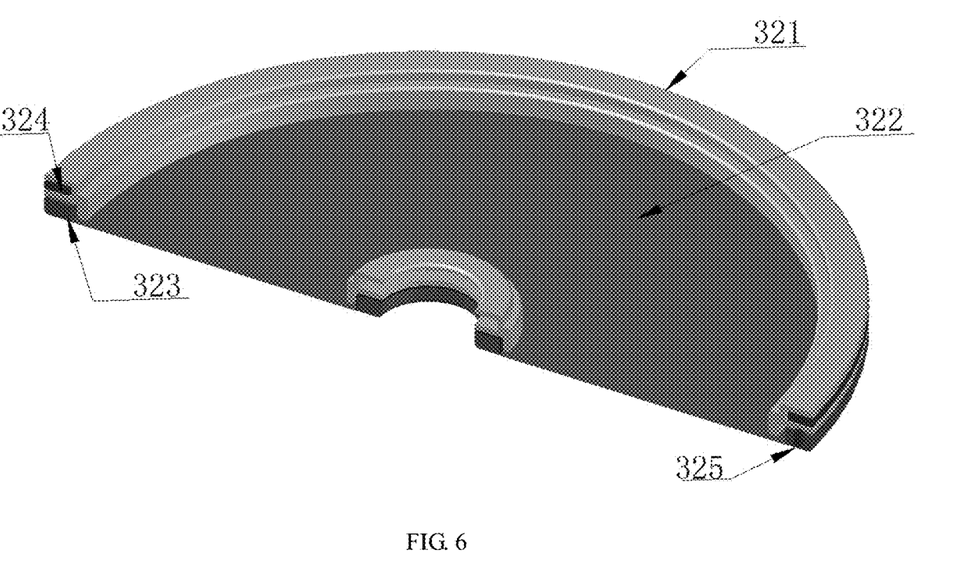
FIG. 6 shows the structure of a rubber piston.

Thus, in some other embodiments, as shown in FIG. 4 to FIG. 6, a displacement sensor fixing plate 30 is disposed inside the reactor body 10, a plurality of displacement sensors 31 are evenly disposed wherein one end of each displacement sensor 31 is fixed to the displacement sensor fixing plate 30 and the other end of each displacement sensor 31 is stretchably and sealingly fixed to a rubber piston 32, and the rubber piston 32 is tightly attached to the superstratum layer 1001.

With such configuration, deformation will take place when natural gas hydrate dissociation occurs in the sediment layer, affecting stability of the superstratum layer and causing shape change of the superstratum layer; the rubber piston, which connect the displacement sensors and the superstratum layer, will change its shape along with the deformation of the superstratum layer, which therefore accurately transmits the subsidence deformation of the superstratum layer to the displacement sensors.

For a large-scale natural gas hydrate experimental system, the constructed formation will be large in area while the dissociation of natural gas hydrates involves uncertainties, and therefore subsidence deformation will not be uniform throughout entire area. Since sufficient displacement sensors are connected to the rubber piston over the superstratum layer, which allows the measurement of subsidence deformation at each spot, and therefore realizes the measurement of stratum deformation throughout a large area. By combining the subsidence deformation data of all spots to form an uneven surface from the underlying deformation, it is possible to overcome the limitation of measurements in only one dimension and realize the three-dimensional measurements of stratum deformation.

The rubber piston 32 comprises a piston frame 321 and a rubber piston plate 322 whose periphery is sealingly fixed to the piston frame 321. The rubber piston further comprises a rubber insert 323, a piston gasket 324, and a clip 325; the piston gasket 324 is embedded in a groove of the piston frame 321; the periphery of the rubber piston plate 322 is sealingly fixed to a lower surface of the piston frame 321 through the rubber insert 323, and the clip 325 is embedded in the rubber insert 323. In the case of large-scale subsidence, if the periphery of the rubber piston plate 322 is fixed, the extent of deformation may reach or even exceed the deformation limit of the rubber piston plate 322, such that it is impossible to precisely measure the stratum deformation, or even, the rubber piston plate will be damaged. Thus, in the present embodiment, the periphery of the rubber piston plate 322 is sealingly fixed to the piston frame 321 having the piston gasket 324; when the scale of subsidence is large, the rubber piston plate 322 will compress the rubber insert 323, and the rubber insert 323, through the non-metallic clip 325, pulls the piston frame 321 to reciprocate; thereby the displacement measured by each displacement sensor 31 is the displacement of the piston plus the displacement of each spot on the rubber piston plate 322, which greatly increases the measurement range of stratum subsidence, or in other words, enables the precise measurement of stratum deformation of large-scale subsidence.

Specifically, the displacement sensors 31 are high-accuracy LVDT displacement sensors, Abek LCA50. Measurement range: 0 to 50 mm. Measurement resolution: 0.001 mm. Measurement accuracy: <±0.2% FS.

Accordingly, compared with the prior art, the technical solution as shown in FIG. 4 to FIG. 6 has the following technical advantages:

(1) The device, provided with the sufficient displacement sensors, enables the measurement of stratum deformation caused by large-scale dissociation of natural gas hydrates.

(2) The measurement range is high, which is the sum of the piston range and the elastic limit of the rubber piston plate.

(3) The device enables the measurement of curved surface of stratum deformation caused by natural gas hydrate dissociation, so as to realize a three-dimensional measurement of stratum deformation, since it is provided with multiple measurement spots while the rubber piston plate which is sufficiently flexible and thin realizes separate measurement of each spot.

(4) The device has high tightness and is resistant to high pressure, and thereby it will not affect the natural gas hydrate experimental system; since the rubber piston plate is resistant to high pressure, the piston gasket can provide effective tightness during reciprocating motion of the piston frame.

(5) The natural gas hydrate experimental system has improved in safety, as the design of rubber piston not only increases the measurement range, but also provides effective protection to the rubber piston plate. Without such design, when the scale of stratum deformation is large, the rubber piston plate will be excessively deformed, and will be even destroyed when it reaches the elastic limit, resulting in damage to the experimental system.

(6) The measurement accuracy is improved. Such improvement is realized through the increased amount of measurement spots, and also through the design of rubber piston which effectively improves the measurement accuracy when the extent of subsidence reaches the elastic limit of the rubber piston plate where the rubber piston plate may fail to sensitively reflect the subsidence.

Furthermore, though the flow filed measurement is useful and necessary for large-scale experimental systems for studying natural gas hydrate, it is still difficult to realize. At present, devices for measuring flow field are mostly designed to allow visual inspection, such as providing optical generators in combination with cameras or disposing visual units such as sight glasses, for observing or filming the change of flow field and thereby realize the measurement of flow field. However, natural gas hydrates are mostly accumulated in porous media, wherein use of sight glasses only enables observation of the porous media, while it is difficult to send a camera deep into a reactor and film in the environment inside the reactor. It is impossible to effectively observe or measure the flow field in the reactor by these means.

Figure 7:
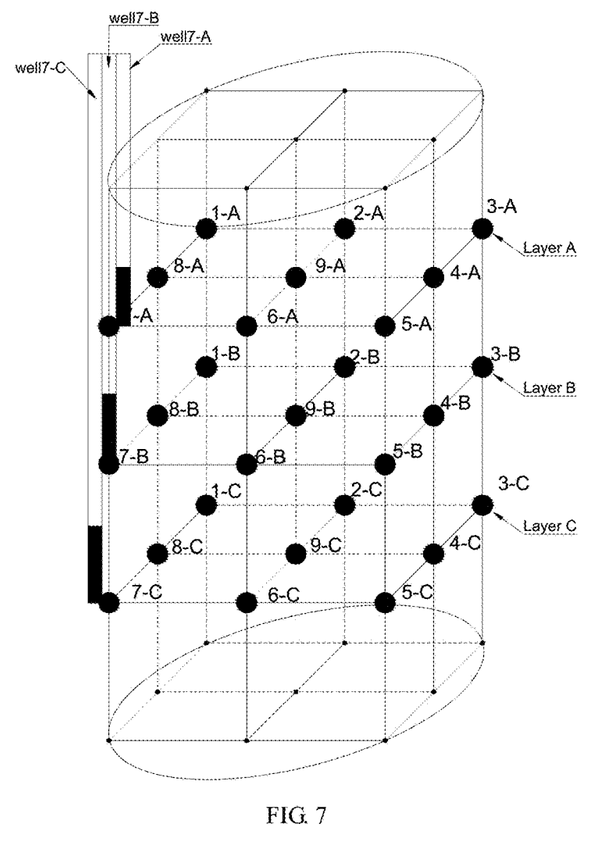
FIG. 7 shows the distribution of wells in the reactor in one embodiment.

Therefore, in some embodiments, as shown in FIG. 7, nine vertical wells are symmetrically distributed throughout each layer in the reactor body. The wells are respectively numbered as 1-A, 2-A, . . . , 9-B, and 9-C, wherein the vertical well 9-B located at center is a central vertical well, while the remaining vertical wells are non-central vertical wells.

Figure 8:
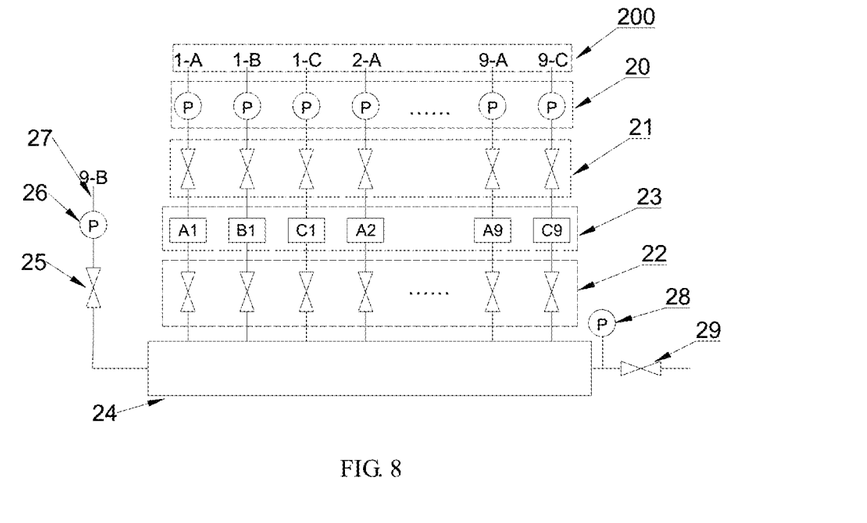
FIG. 8 shows the composition of a flow field measurement device.

As shown in FIG. 8, all non-central vertical well outlet pipelines 200, except for the vertical well 9-B, are respectively connected to a non-central vertical well pressure sensor 20, a non-central vertical well outlet valve 21, and one end of a differential pressure sensor 23 in sequence. The other end of the differential pressure sensor 23 is connected to a communicating vessel valve 22. All of the communicating vessel valves 22 are connected with the communicating vessel 24. The other end of the communicating vessel 24 is connected to the central vertical well outlet valve 25, the central vertical well pressure sensor 26, and a central vertical well outlet pipeline 27.

The twenty-six differential pressure sensors are respectively numbered as A1, B1, C1, A2, . . . , A9, and C9, representing the differential pressure sensor connecting the well 1-A and well 9-B, the differential pressure sensor connecting the well 1-B and well 9-B, . . . , the differential pressure sensor connecting the well 9-A and well 9-B, and the differential pressure sensor connecting the well 9-C and well 9-B. Specifically, the differential pressure sensors 23 have a measuring accuracy higher than that of the central vertical well pressure sensor 26 and non-central vertical well pressure sensors 20, and a measuring range lower than that of the central vertical well pressure sensor 26 and non-central vertical well pressure sensors 20. Since the pressure sensors are not applicable for low pressure differences due to their low measuring accuracy while the differential pressure sensors 23 have a higher measuring accuracy, when the pressure difference is relatively low, the pressure sensors may show the same readings while the differential pressure sensors is capable of revealing the pressure difference; when the pressure difference is relatively high and exceed the measuring range of the differential pressure sensors, the differential pressure sensors may be damaged. In summary, the differential pressure sensors have a high accuracy but a low measuring range, while the pressure sensors have a high measuring range but a low accuracy, and thus these two kinds of sensors should be used in combination.

Accordingly, when it is necessary to inspect a flow field in the reactor, the first step is recording readings of the twenty-seven pressure sensors to obtain a pressure difference between each vertical well and the central vertical well, and then comparing the obtained pressure difference with a measuring range of the differential pressure sensor; if the obtained pressure difference is higher than the measuring range of the differential pressure sensor, then the obtained pressure difference is determined to be a pressure difference between the non-central vertical well corresponding to the differential pressure sensor and the central vertical well; if the obtained pressure difference is not higher than the measuring range of the differential pressure sensor, then opening the non-central vertical well outlet valve and the communicating vessel valve which are connected to the differential pressure sensor, and measuring the pressure difference between the corresponding non-central vertical well and the central vertical well using the differential pressure sensor. Driven by the pressure differences, gas and liquid will flow spontaneously from a high pressure zone to a low pressure zone (or tend to flow spontaneously from the high pressure zone to the low pressure zone), in other words, the accurate measurement of flow field in the reactor is realized.

In view of the above, with the flow field measurement device, the flow field inside the reactor is quantified according to the pressure differences between the points, accurately and effectively. Providing differential pressure sensors, between a measuring point of the central vertical well and a measuring point of each of the non-central vertical wells, to measure the pressure differences, enables reasonable distribution of three-dimensional space inside the entire reactor, making it easier to analyze the gas-liquid flow trends in the reactor with the simulated flow field. The step of determining whether to turn on the differential pressure sensors according to a predetermination based on the feedback from the pressure sensors, allows flow field measurements in the reactor under both high and low pressure differences and effective protection of the differential pressure sensors. Meanwhile, since communication of the entire measurement device is realized by the vertical well outlet pipelines, the measurement device can be externally connected to the reactor, in other words, the differential pressure sensors and the communicating vessel can be disposed outside the reactor. Thus, it is not necessary to conduct significant modifications to the entire gas hydrate system, and no damage will be done to the experimental devices; for a natural gas hydrate experimental system without flow field measurement function, it is possible to introduce the present device whenever it is required.

Specifically, a data output of each of the non-central vertical well pressure sensors 20, the central vertical well pressure sensor 26, and the differential pressure sensors 23 is connected to a data collecting-processing-displaying module 4. With such configuration, the data collecting-processing-displaying module 4 enables the real-time display of the recorded data, so as to realize the real-time measurements of flow field in the reactor.

Preferably, the communicating vessel 24 is further provided with a communicating vessel pressure sensor 28 and a gas injection valve 29. Such configuration allows testing the differential pressure sensors 23 using the gas injection valve 29. The method are as follows: closing the non-central vertical well outlet valves, such that the differential pressure sensors show a same reading at their ends connected to the non-central vertical well outlet valves; connecting the gas injection valve of the communicating vessel to a gas cylinder with a given pressure lower than the measuring range of the differential pressure sensors; opening the communicating vessel valves, and opening a valve of the gas cylinder, and recording readings of the differential pressure sensors. Normally, the readings of the differential pressure sensors should be identical; a differential pressure sensor that shows no reading or a significantly different reading requires replacement or repair.

Accordingly, compared with the prior art, the technical solution as shown in FIG. 7 to FIG. 8 has the following technical advantages:

(1) The pressure sensors and the differential pressure sensors are connected to the data collecting-processing-displaying module, which realizes the real-time measurements of flow field in the reactor.

(2) The flow field inside the reactor is quantified according to the pressure differences between the points in the reactor, accurately and effectively.

(3) Providing differential pressure sensors, between a measuring point of the central vertical well and a measuring point of each of the non-central vertical wells, to measure the pressure differences, enables reasonable distribution of three-dimensional space inside the entire reactor, making it easier to analyze the gas-liquid flow trends in the reactor with the simulated flow field.

(4) The step of determining whether to turn on the differential pressure sensors according to a predetermination based on the feedback from the pressure sensors, allows flow field measurements in the reactor under both high and low pressure differences and effective protection of the differential pressure sensors.

(5) The differential pressure sensors are externally disposed for flow field measurements in the reactor; such design will not affect the natural gas hydrate experiment.

(6) It is not necessary to conduct significant modifications to the entire gas hydrate system, and no damage will be done to the experimental devices; for a natural gas hydrate experimental system without flow field measurement function, it is possible to introduce the present device whenever it is required.

(7) Design of the communicating vessel allows testing the differential pressure sensors regardless of the natural gas hydrate experimental system, and thereby the operation is simple, safe, and reliable.

In addition, since currently existing natural gas hydrate experimental devices are constructed, as compared with actual formation environment, in a scale not enough to present a temperature gradient, most reactors are configured to be disposed in a constant temperature water bath. However, in actual exploitation, natural gas hydrate reservoirs are affected by the temperature of the formation, and there will be certain temperature differences and temperature gradient as the temperature changes with depth. The temperature gradient will have a certain impact on the formation and exploitation of natural gas hydrates, resulting in a higher requirement, for simulating the formation temperature gradient, on large-scale natural gas hydrate devices which operate in a situation closer to the actual exploitation; how to accurately regulate the temperature gradient to realize the in-situ temperature field simulation of NGH reservoir is a technical problem to be solved at present.

Figure 9:
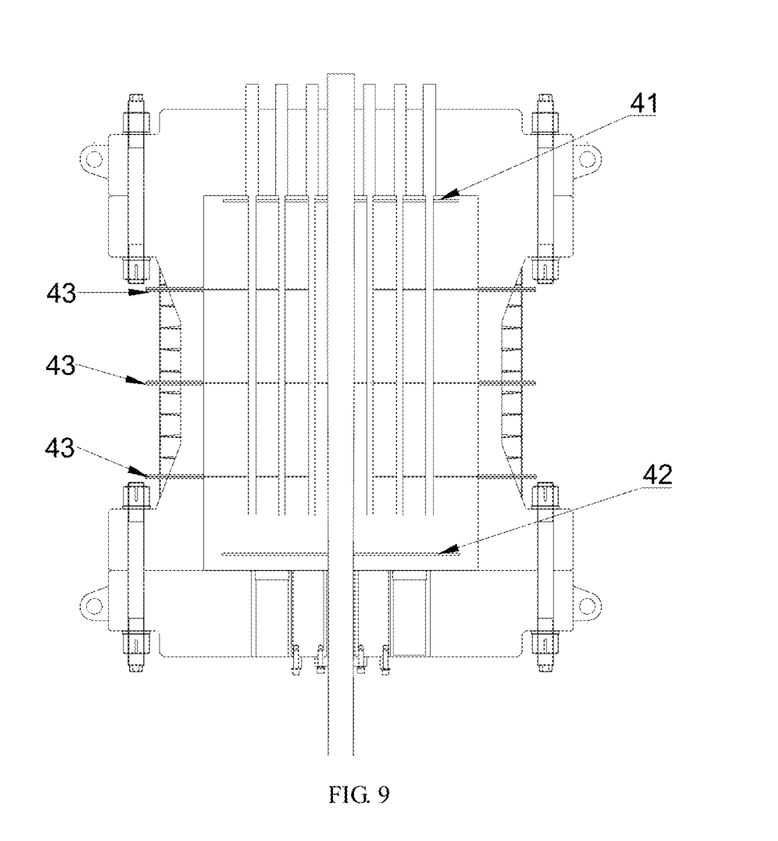
FIG. 9 shows the structure of a reactor in one embodiment.
Figure 10:
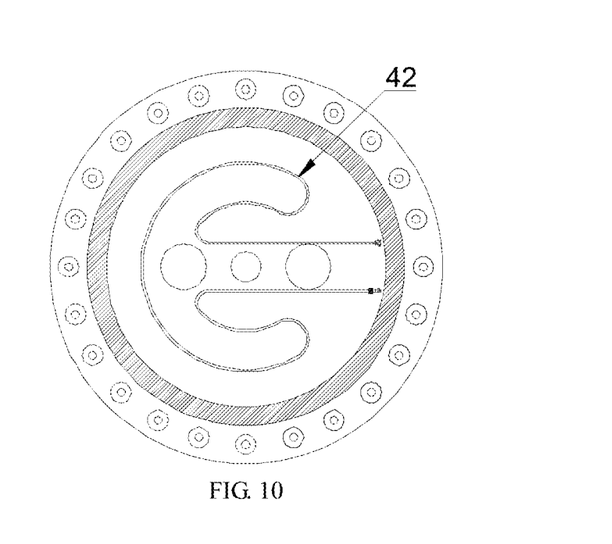
FIG. 10 shows the disposition of an upper circulation coil.
Figure 11:
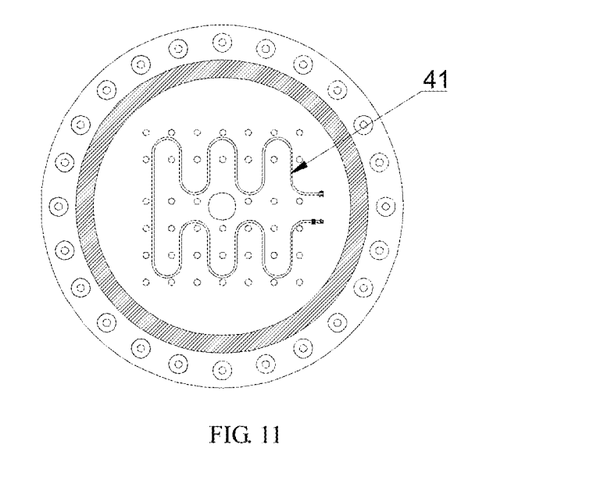
FIG. 11 shows the disposition of a lower circulation coil.

Accordingly, as shown in FIG. 9 to FIG. 11, an upper circulation coil 41 and a lower circulation coil 42 are respectively disposed at an upper end and a lower end inside the reactor body. The upper circulation coil 41 and the lower circulation coil 42 are respectively provided with an independent heat exchange device (not shown in the drawings) to realize the circulation of the heat transfer medium in the coils. The heat exchange devices are capable of cooling, heating, and maintaining temperature. With the upper circulation coil 41 and the lower circulation coil 42, isothermal planes are formed at the upper end and the lower end inside the reactor body. However, with the isothermal planes formed at the upper end and the lower end inside the reactor body only, since heat insulation at the periphery of the reactor is not realized, under the influence of thermal convection, the temperature will be high throughout most of the space from bottom to top, making it impossible to form a balanced temperature gradient, and therefore failing to simulate the temperature gradient throughout the formation. Accordingly, in the present embodiment, N temperature control pipes 43 are spacedly provided inside the reactor body 10 and between the upper circulation coil 41 and the lower circulation coil 42, configured to form a vertical temperature gradient in the reactor body 10, wherein N is a positive integer and determined depending on actual requirement. In come embodiments, N is 3, i.e., three temperature control pipes 43 are provided, and each temperature control pipe 43 is also provided with an independent heat exchange device to realize the circulation of the heat transfer medium in the temperature control pipe.

The configuration of providing the upper circulation coil and the lower circulation coil at the upper and lower ends inside the reactor body realizes stable heating. N temperature control pipes are spacedly provided between the upper circulation coil and the lower circulation coil and encircling the reactor body; moreover, each temperature control pipe is also provided with an independent heat exchange device to realize the circulation of the heat transfer medium in the temperature control pipe (i.e., they are also capable of cooling, heating, and maintaining temperature), such that the temperature of each temperature control pipe can be regulated independently, realizing the simulation of formation temperature gradient inside the reactor body.

In addition, since the formation temperature gradually decreases at a certain gradient from bottom to top, in order to realize a more precise simulation of formation temperature gradient, the N temperature control pipes are equally spaced from bottom to top and a constant temperature difference is given between the temperature control pipes; such configuration the arrangement of low temperature zone to high temperature zone at intervals of the same temperature difference and distance from top to bottom. Specifically, the lower circulation coil 42 is set to produce a high temperature T1, while the upper circulation coil 41 is set to produce a low temperature T2; N temperature control pipes 43 are provided, wherein the temperature difference between the temperature control pipes 43 can be expressed as $\Delta T=(T1-T2)/(N+1)$, i.e., the temperature control pipes 43 from top to bottom are respectively set to produce a temperature of $T2+\Delta T$, $T2+2\Delta T$, and $T2+N\Delta T$.

Moreover, in order to maintain the temperature difference $\Delta T$ between the temperature control pipes stable in real time so as to achieve the most realistic simulation of the formation, temperature sensors are provided inside the reactor body 10, configured to monitor the temperatures of the upper circulation coil 41, the lower circulation coil 42 and the N temperature control pipes 43 and transmit the monitored temperature data to the temperature regulating module. The temperature regulating module regulates in real time the operation of each heat exchange device according to the monitored temperature data, so as to maintain the vertical temperature gradient in the reactor body stable. Specifically in the present embodiment, the temperature difference for the vertical temperature gradient is set to be 5° C., and the temperature control accuracy is ±0.5° C.

Preferably, the lower circulation coil 42 is disposed inside the reactor body as shown in FIG. 10, wherein it is kept away from the wells and holes while ensures uniform heating by means of water bath. Similarly, the upper circulation coil 41 is disposed inside the reactor body as shown in FIG. 11, wherein it is kept away from the wells, holes and measuring points while ensures uniform heating.

Accordingly, compared with the prior art, the technical solution as shown in FIG. 9 to FIG. 11 has the following technical advantages:

(1) The upper and lower circulation coils ensure uniform heating while do not affect other operations performed in the reactor, such as introducing liquid and gas.

(2) The upper and lower circulation coils are respectively provided with an independent heat exchange device to realize the circulation, such that they can operate simultaneously and are capable of cooling, heating, and maintaining temperature.

(3) The temperature control pipes are respectively provided with an independent heat exchange device, such that they can operate simultaneously and are capable of cooling, heating, and maintaining temperature.

(4) The vertical temperature gradient is regulated based on signal feedback from the temperature sensors inside the reactor, so as to maintain the temperature gradient in the reactor body stable in real time, achieving a better simulation.

(5) The temperature gradient simulation allows accurately regulating the temperature gradient to realize the in-situ temperature field simulation of NGH reservoir.

In view of the above, compared with the prior art, the system of the present invention has the following technical advantages:

(1) The system enables preparing a natural gas hydrate sample and simulating environment for forming a natural gas hydrate reservoir in 3,000-meter-deep seafloor sediments at South China Sea.

(2) The system allows simulation study for the depressurization method and the thermal stimulation method under various well arrangements.

(3) Exploitation researches with full-sized wells are realized for optimizing well structures and studying sand production and prevention.

(4) The system enables the study on hydrate dissociation, liquid-gas flow, heat transfer, and sediment stability mechanism.

The above-mentioned embodiments are only intended to illustrate the technical concept and characteristics of the present invention, enabling those of ordinary skill in the art to understand the content of the present invention and implement them accordingly, but are not intended to limit the scope of the present invention. All equivalent changes or modifications made according to the essence of the present invention should fall within the scope of the present invention.

What is claimed is:

1. A comprehensive three-dimensional exploitation experimental system for large-scale and full-sized exploitation wells, comprising:
    a reactor, wherein the reactor is configured to prepare a natural gas hydrate sample, for simulating an environment for forming a natural gas hydrate reservoir in seafloor sediments, wherein the reactor comprises a reactor body, an upper cover disposed at an upper surface of the reactor body, and a lower cover disposed at a lower surface of the reactor body;
    a gas introducing module, wherein the gas introducing module is configured to introduce a gas to the reactor during a hydrate formation;
    a liquid introducing module, wherein the liquid introducing module is configured to introduce liquid to the reactor during the hydrate formation;
    a temperature regulating module, wherein the temperature regulating module is configured to regulate a temperature in the reactor; and
    a data-collecting-processing-displaying module, configured to collect, store, process and display data of the comprehensive three-dimensional exploitation experimental system during an experiment, wherein:
    an upper circulation coil and a lower circulation coil are respectively disposed at an upper end and a lower end inside the reactor body, wherein the upper circulation coil and the lower circulation coil respectively include an independent heat exchange device to realize a circulation of a heat transfer medium in the upper circulation coil and the lower circulation coil:
    N temperature control pipes are spacedly disposed inside the reactor body and between the upper circulation coil and the lower circulation coil, wherein the N temperature control pipes are configured to form a vertical temperature gradient in the reactor body, wherein N is a positive integer; and
    each of the N temperature control pipes also includes an independent heat exchange device to realize the circulation of the heat transfer medium in the each of the N temperature control pipes.

2. The comprehensive three-dimensional exploitation experimental system of claim 1, wherein
    a central vertical well is disposed at a center and throughout a vertical direction of the reactor, and holes are spacedly disposed on the central vertical well along a longitudinal direction of the central vertical well inside the reactor;

a directional-control ball valve is disposed, at an upper portion of the central vertical well, the directional-control ball valve being disposed outside the reactor, and one outlet of the directional-control ball valve is connected to a central vertical well discharge pipeline;

a sight glass is disposed on the central vertical well discharge pipeline, wherein a first camera and a first lamp are disposed beside the sight glass;

an endoscopic-camera tube is disposed inside the central vertical well, passing through the directional-control ball valve, and extending to an outside of the central vertical well;

a second camera and a second lamp are disposed at a bottom end of the endoscopic-camera tube, wherein the second lamp is disposed above the second camera and arranged obliquely;

wherein the first camera is configured to send images captured by the first camera to the data-collecting-processing display module, and wherein the second camera is configured to send images captured by the second camera to the data-collecting-processing-displaying module;

a mechanical sensor is disposed at the bottom end of the endoscopic-camera tube, wherein data measured by the mechanical sensor is sent to the data-collecting-processing-displaying module; and a scaled sight glass for observing settled sands is disposed on the central vertical well and outside the reactor.

3. The comprehensive three-dimensional exploitation experimental system of claim 1, wherein an inside of the reactor body is divided into a plurality of layers from top to bottom, wherein a plurality of vertical wells are disposed throughout each layer of the plurality of layers, the plurality of vertical wells comprises a central vertical well located at a center and non-central vertical wells are remainders;

each of the non-central vertical wells includes non-central vertical well outlet pipelines, Wherein each of the non-central vertical well outlet pipelines is correspondingly includes one non-central vertical well pressure sensor, one non-central vertical well outlet valve, one differential pressure sensor, and one communicating vessel valve, the non-central vertical well pressure sensor, the non-central vertical well outlet valve and the differential pressure sensor communicate in sequence, and the communicating vessel valves are connected to a communicating vessel;

the non-central vertical well pressure sensors, the non-central vertical well outlet valves, the differential pressure sensors, and the communicating vessel valves each being equal in number to a number of the non-central vertical wells;

the central vertical well includes a central vertical well outlet pipeline, wherein the central vertical well outlet pipeline includes a central vertical well pressure sensor and a central vertical well outlet valve, the central vertical well pressure sensor and the central vertical well outlet valve communicate in sequence, and the central vertical well outlet valve is connected to the communicating vessel;

a data output of each of the non-central vertical well pressure sensors, the central vertical well pressure sensor, and the differential pressure sensors is connected to the data-collecting-processing-displaying module; and the differential pressure sensors have a measuring accuracy higher than a measuring accuracy of the central vertical well pressure sensor and a measuring accuracy of the non-central vertical well pressure sensors, and a measuring range lower than a measuring range of the central vertical well pressure sensor and a measuring range of the non-central vertical well pressure sensors.

4. The comprehensive three-dimensional exploitation experimental system of claim 3, wherein the communicating vessel further comprises a communicating vessel pressure sensor and a gas injection valve.

5. The comprehensive three-dimensional exploitation experimental system of claim 1, wherein the N temperature control pipes are equally spaced from bottom to top and a constant temperature difference is given between the N temperature control pipes, wherein the constant temperature difference is expressed as:

$\Delta T=(T1-T2)/(N+1)$, wherein T2 represents a temperature of the lower circulation coil, and T1 represents a temperature of the upper circulation coil.

6. The comprehensive three-dimensional exploitation experimental system of claim 5, wherein the reactor body further comprises temperature sensors, the temperature sensors disposed inside the reactor body and configured to monitor the temperature of the upper circulation coil, the temperature of the lower circulation coil and temperatures of the N temperature control pipes, and the temperature sensors transmit monitored temperature data to the temperature regulating module; and the temperature regulating module is configured to regulate an operation of each heat exchange device according to the monitored temperature data in real time to maintain the vertical temperature gradient in the reactor body stable.

7. The comprehensive three-dimensional exploitation experimental system of claim 1, wherein a plurality of layers inside the reactor body comprise a superstratum layer, a sediment layer and a substratum layer from top to bottom, and a displacement sensor fixing plate is disposed inside the reactor body;

a plurality of displacement sensors are evenly disposed, wherein a first end of each displacement sensor is fixed to the displacement sensor fixing plate and a second end of the each displacement sensor is stretchably and sealingly fixed to a rubber piston, and the rubber piston is attached to the superstratum layer; and the plurality of displacement sensors are configured to send monitored data to the data-collecting-processing-displaying module.

8. The comprehensive three-dimensional exploitation experimental system of claim 7, wherein the rubber piston comprises a piston frame and a rubber piston plate, wherein a periphery of the rubber piston plate is sealingly fixed to the piston frame;

the rubber piston further comprises a rubber insert, a piston gasket, and a clip;

the piston gasket is embedded in a groove of the piston frame;

the periphery of the rubber piston plate is sealingly fixed to a lower surface of the piston frame through the rubber insert; and the clip is embedded in the rubber insert.

9. The comprehensive three-dimensional exploitation experimental system of claim 1, further comprising a gas production module;

the gas production module is configured to control a depressurization range and a depressurization rate inside the reactor, and conduct a gas-liquid-sand separation and measurement during a hydrate exploitation;

the gas introducing module comprises a natural gas supply, a booster pump, a gas flow meter, and a gas valve, wherein the natural gas supply, the booster pump, the gas flow meter and the gas valve are connected sequentially, wherein an outlet of the gas valve is connected to the reactor; and the liquid introducing module comprises a liquid supply, a liquid introducing pump, a temperature regulator, and a liquid valve, wherein the liquid supply, the liquid introducing pump, the temperature regulator and the liquid valve are connected sequentially, wherein an outlet of the liquid valve is connected to the reactor.

10. A comprehensive three-dimensional exploitation experimental system for large-scale and full-sized exploitation wells, comprising:

a reactor, Wherein the reactor is configured to prepare a natural gas hydrate sample, for simulating an environment for forming a natural gas hydrate reservoir in seafloor sediments, wherein the reactor comprises a reactor body, an upper cover disposed at an upper surface of the reactor body, and a lower cover disposed at a lower surface of the reactor body;

a gas introducing module, wherein the gas introducing module is configured to introduce a gas to the reactor during a hydrate formation;

a liquid introducing module, wherein the liquid introducing module is configured to introduce liquid to the reactor during the hydrate formation;

a temperature regulating module, wherein the temperature regulating module is configured to regulate a temperature in the reactor;

a data-collecting-processing-displaying module, configured to collect, store, process and display data of the comprehensive three-dimensional exploitation experimental system during an experiment;

a gas production module, the gas production module being configured to control a depressurization range and a depressurization rate inside the reactor, and conduct a gas-liquid-sand separation and measurement during a hydrate exploitation;

the gas introducing module comprising a natural gas supply, a booster pump, a gas flow meter, and a gas valve, wherein the natural gas supply, the booster pump, the gas flow meter and the gas valve are connected sequentially, wherein an outlet of the gas valve is connected to the reactor; and the liquid introducing module comprises a liquid supply, a liquid introducing pump, a temperature regulator, and a liquid valve, wherein the liquid supply, the liquid introducing pump, the temperature regulator and the liquid valve are connected, wherein an outlet of the liquid valve is connected to the reactor.

11. The comprehensive three-dimensional exploitation experimental system of claim 10, wherein a central vertical well is disposed at a center and throughout a vertical direction of the reactor, and holes are spacedly disposed on the central vertical well along a longitudinal direction of the central vertical well inside the reactor;

a directional-control ball valve is disposed, at an upper portion of the central vertical well, the directional-control ball valve being disposed outside the reactor, and one outlet of the directional-control ball valve is connected to a central vertical well discharge pipeline;

a sight glass is disposed on the central vertical well discharge pipeline, wherein a first camera and a first lamp are disposed beside the sight glass;

an endoscopic-camera tube is disposed inside the central vertical well, passing through the directional-control ball valve, and extending to an outside of the central vertical well;

a second camera and a second lamp are disposed at a bottom end of the endoscopic-camera tube, wherein the second lamp is disposed above the second camera and arranged obliquely;

wherein the first camera is configured to send images captured by the first camera to the data-collecting-processing-displaying module and wherein the second camera is configured to send images captured by the second camera to the data-collecting-processing-displaying module;

a mechanical sensor is included at the bottom end of the endoscopic-camera tube, wherein data measured by the mechanical sensor is sent to the data-collecting-processing-displaying module; and a scaled sight glass for observing settled sands is disposed on the central vertical well and outside the reactor.

12. The comprehensive three-dimensional exploitation experimental system of claim 10, wherein an inside of the reactor body is divided into a plurality of layers from top to bottom, wherein a plurality of vertical wells are disposed throughout each layer of the plurality of layers, the plurality of vertical wells comprises a central vertical well located at a center and non-central vertical wells are remainders;

each of the non-central vertical wells includes non-central vertical well outlet pipelines, wherein each of the non-central vertical well outlet pipelines correspondingly includes one non-central vertical well pressure sensor, one non-central vertical well outlet valve, one differential pressure sensor, and one communicating vessel valve, the non-central vertical well pressure sensor, the non-central vertical well outlet valve and the differential pressure sensor communicate in sequence, and the communicating vessel valves are connected to a communicating vessel;

the non-central vertical well pressure sensors, the non-central vertical well outlet valves, the differential pressure sensors, and the communicating vessel valves each being equal in number to a number of the non-central vertical wells;

the central vertical well includes a central vertical well outlet pipeline, wherein the central vertical well outlet pipeline includes a central vertical well pressure sensor and a central vertical well outlet valve, the central vertical well pressure sensor and the central vertical well outlet valve communicate in sequence, and the central vertical well outlet valve is connected to the communicating vessel;

a data output of each of the non-central vertical well pressure sensors, the central vertical well pressure sensor, and the differential pressure sensors is connected to the data-collecting-processing-displaying module; and the differential pressure sensors have a measuring accuracy higher than a measuring accuracy of the central vertical well pressure sensor and a measuring accuracy of the non-central vertical well pressure sensors, and a measuring range lower than a measuring range of the central vertical well pressure sensor and a measuring range of the non-central vertical well pressure sensors.

13. The comprehensive three-dimensional exploitation experimental system of claim 12, wherein the communicating vessel further comprises a communicating vessel pressure sensor and a gas injection valve.

14. The comprehensive three-dimensional exploitation experimental system of claim 10 wherein:
- an upper circulation coil and a lower circulation coil are respectively disposed at an upper end and a lower end inside the reactor body, wherein the upper circulation coil and the lower circulation coil respectively include an independent heat exchange device to realize a circulation of a heat transfer medium in the upper circulation coil and the lower circulation coil;
- N temperature control pipes are spacedly disposed inside the reactor body and between the upper circulation coil and the lower circulation coil, wherein the N temperature control pipes are configured to form a vertical temperature gradient in the reactor body, wherein N is a positive integer; and
- each of the N temperature control pipes also includes an independent heat exchange device to realize the circulation of the heat transfer medium in the each of the N temperature control pipes.

15. The comprehensive three-dimensional exploitation experimental system of claim 14, wherein
- the N temperature control pipes are equally spaced from bottom to top and a constant temperature difference is given between the N temperature control pipes, wherein the constant temperature difference is expressed as:
- $\Delta T=(T1-T2)/(N+1)$, wherein T2 represents a temperature of the lower circulation coil, and T1 represents a temperature of the upper circulation coil.

16. The comprehensive three-dimensional exploitation experimental system of claim 15, wherein
- the reactor body further comprises temperature sensors, the temperature sensors disposed inside the reactor body and configured to monitor the temperature of the upper circulation coil, the temperature of the lower circulation coil and temperatures of the N temperature control pipes, and the temperature sensors transmit monitored temperature data to the temperature regulating module; and
- the temperature regulating module is configured to regulate an operation of each heat exchange device according to the monitored temperature data in real time to maintain the vertical temperature gradient in the reactor body stable.

17. The comprehensive three-dimensional exploitation experimental system of claim 10, wherein
- a plurality of layers inside the reactor body comprise a superstratum layer; a sediment layer and a substratum layer from top to bottom, and a displacement sensor fixing plate is disposed inside the reactor body;
- a plurality of displacement sensors are evenly disposed, wherein a first end of each displacement sensor is fixed to the displacement sensor fixing plate and a second end of the each displacement sensor is stretchably and sealingly fixed to a rubber piston, and the rubber piston is attached to the superstratum layer; and
- the plurality of displacement sensors are configured to send monitored data to the data-collecting-processing-displaying module.

18. The comprehensive three-dimensional exploitation experimental system of claim 17, wherein
- the rubber piston comprises a piston frame and a rubber piston plate, wherein a periphery of the rubber piston plate is sealingly fixed to the piston frame;
- the rubber piston further comprises a rubber insert, a piston gasket, and a clip;
- the piston gasket is embedded in a groove of the piston frame;
- the periphery of the rubber piston plate is sealingly fixed to a lower surface of the piston frame through the rubber insert; and
- the clip is embedded in the rubber insert.

* * * * *